United States Patent [19]

Laurila et al.

[11] Patent Number: 5,065,416
[45] Date of Patent: Nov. 12, 1991

[54] ON-LINE SLURRY ASH MONITORING SYSTEM

[75] Inventors: Melvin J. Laurila, Laurium; Robert J. Brown, Calumet; Robert C. Greenlund, Hancock, all of Mich.

[73] Assignee: Process Technology, Inc., Calumet, Mich.

[21] Appl. No.: 407,201

[22] Filed: Sep. 14, 1989

Related U.S. Application Data

[63] Continuation-in-part of Ser. No. 128,648, Dec. 4, 1987.
[51] Int. Cl.$^5$ .................... G01N 23/06; G01N 23/223
[52] U.S. Cl. .......................... 378/53; 378/45; 378/83; 378/51
[58] Field of Search ................... 378/44, 45, 47, 83, 378/51-54; 250/255, 304

[56] References Cited
U.S. PATENT DOCUMENTS 4,282,434  8/1981  Lyman ................... 378/53
4,388,530  6/1983  Lubecki et al. ........... 378/45
4,450,576  5/1984  Lubecki et al. ........... 378/47
4,486,894 12/1984  Page et al. .............. 250/255

*Primary Examiner*—Edward P. Westin
*Assistant Examiner*—Don Wong
*Attorney, Agent, or Firm*—Harness, Dickey & Pierce

[57] ABSTRACT

An on-line slurry ash monitoring system for evaluating the composition of coal slurries in coal preparation plants. A coal slurry is introduced into a sample reservoir where it is removed and passed through a closed loop slurry transport system which causes the sample to be directed through a sensor and recirculated back to the reservoir. In order to enhance sensor accuracy, a sample is exposed to vacuum pressure conditions which removes gas bubbles and dissolved gases from the sample. The sensor is preferably a radiation absorption type in which characteristic absorptions of coal particles, ash and iron are evaluated by associated electronics to provide an output of slurry composition.

20 Claims, 3 Drawing Sheets

ON-LINE SLURRY ASH MONITORING SYSTEM

CROSS-REFERENCE TO RELATED APPLICATION

This application is a continuation-in-part of application Ser. No. 128,648, filed on Dec. 4, 1987 and assigned to the assignee of this application.

BACKGROUND AND SUMMARY OF THE INVENTION

This invention relates to a system for evaluating a slurry and particularly to such a device for measuring the concentration of ash producing constituents of a coal slurry.

In a typical coal preparation plant, coal is processed in an aqueous medium to permit the separation of carbonaceous material from ash forming minerals in unit operations that exploit differences in physical and/or chemical properties between coal (carbonaceous) particles and impurities. Processors of coal need to evaluate the slurry periodically to ascertain its composition. In particular, the concentration of ash forming minerals in the coal is important to the user and is monitored in order to control the key process variables so that the desired specifications can be met in the end product or "clean" coal.

The standard method of determining ash concentration is prescribed by the American Society for Testing and Materials (ASTM) standard number 3174, which requires a coal sample to be combusted, and an ash determination made to evaluate coal composition. This evaluation process requires a period of time on the order of five hours between initial sample taking and data reduction. Due to this lengthy time requirement, the measurements provided by this method cannot be used in a closed loop process control system as a means of controlling slurry composition or monitoring plant operation.

In order to permit control over plant operations in a more timely manner, various approaches have been considered to enable more rapid assessment of coal slurry composition. One concept involves using detectors which evaluate the slurry by its absorption of radiation in one or more energy bands which is related to its composition. For these systems, a sensor is placed either directly into a slurry sample or mounted on a slurry transport conduit. One particular problem with ash monitoring systems using radiation type detectors is the influence of entrained gas bubbles and dissolved gases which interfere with evaluation accuracy since they generate signal bias, particularly if radiation absorption measurements are taken. The presence of bubbles also adversely affects the measure of the density of the sample. Another shortcoming of such systems is attributable to the fact that they do not sense a homogeneous mixture of slurry or the entire cross section of the slurry, thereby giving rise to additional sources of error.

In one prior art system according to U.S. Pat. No. 4,282,434, issued to Lyman, radiation absorption measurements are taken as a means of determining ash concentration. Lyman also attempts to reduce the effects of entrained gas bubbles within the sample by collapsing them by applying a positive pressure to the sample causing the gas to dissolve into the aqueous medium of the sample. Although the system of Lyman would produce a more accurate density value for the sample by eliminating entrained gases, it does not eliminate the air molecules from the sample. Accordingly, dissolved air within the sample would influence the attenuation of radiation passing through the sample, thereby giving rise to a source of error in the ash determination.

In another prior art system described by U.S. Pat. No. 3,031,571, issued to Fearon, a dry sample is mixed with a stream of liquid mercury. A vacuum is applied to a sample to cause the sample and mercury to be pumped and passed across a sensor. The sensor measures excited X-rays caused by electron bombardment. The Fearon system would not provide an accurate means of evaluating ash concentration and would not allow absorption type sensor systems to be used since the mercury stream would not permit gamma radiation to pass through it.

In addition to the shortcomings of the prior art as discussed above, previously proposed systems including those described by Fearon and Lyman cause the sample to pass across a detector only once which imposes accuracy limitations.

In view of the foregoing, there is a need to provide a slurry ash monitoring system which enables rapid coal slurry evaluation and provides accurate evaluations of slurry composition. In accordance with the present invention, a closed slurry pumping and recirculating system is provided in which a batch of slurry is exposed to vacuum pressure conditions (i.e. pressure less than atmospheric). Exposure to low pressure causes air and other gas bubbles entrained within the slurry to collapse, thereby enabling radiation absorption type detectors to be used to provide accurate measurements without the above mentioned signal bias. Evacuating the gases enhances the accuracy of the measure of density of the sample and further removes dissolved gas which would otherwise absorb radiation and skew measurements when they are present in a dissolved state within the sample. Moreover, the physical configuration of the system according to this invention ensures that a homogeneous slurry mixture passes through the detector.

The system in accordance with this invention also causes the slurry sample batch to be passed through a detector multiple times which gives an average reading for the sample since each particle in the sample has several chances to attenuate the radiation signal. This approach provides enhanced accuracy in evaluating ash concentration. The present system enables slurry samples from multiple sources to be evaluated by a single instrument system.

Radiation absorption type ash analyzers according to the prior art evaluate the concentration of ash producing substances within the coal by evaluating the degree of absorption of a gamma radiation signal passing through the sample. This approach exploits the fact that the mass absorption coefficient for coal is significantly less than that for ash bearing minerals. In accordance with prior art approaches, measurements were taken for radiation of an energy level of 60 Kev or above. Unfortunately, at that energy level, the differences in mass absorption coefficient between coal and ash producing materials are not great, and therefore, these approaches must evaluate relatively small differences in absorption coefficient between these two types of material, giving rise to limitations in the accuracy of measurement. In accordance with this invention, the presence of ash producing materials is evaluated by examining the absorption of radiation at low energy levels, for example, in the 10–30 Kev range.

Irrespective of the energy level used to evaluate ash producing materials within a coal slurry, accuracy limitations are present since all ash producing materials do not behave alike in terms of radiation absorption. In particular, iron pyrite has a disproportionately high absorption characteristic. In accordance with this invention, emissions from the sample of X-ray energy at the 6.4 Kev level is measured and is a stimulated emission from iron pyrite. The measured concentration of pyrite is used to adjust the total ash measurements. Various approaches for measuring the radiation associated with pyrite are described herein. Measurements of iron concentrations in other materials such as iron ore could also be conducted in this manner.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
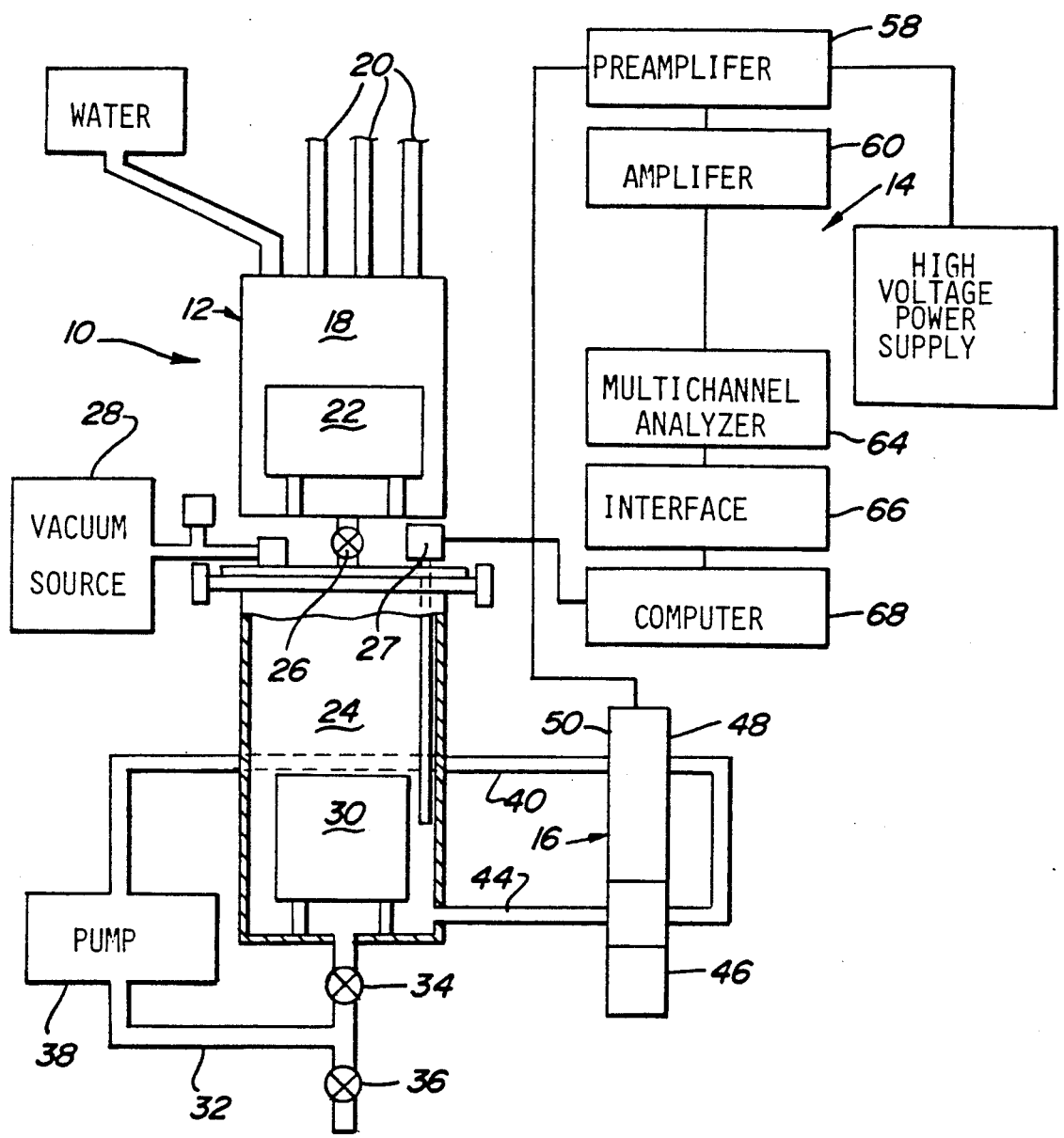
FIG. 1 is a pictorial view of the slurry ash monitoring system in accordance with this invention showing mechanical elements of the system in schematic form and illustrating electrical data processing subsystems in block diagram form.

FIG. 1 illustrates a slurry ash monitoring system in accordance with this invention which is generally designated by reference number 10. Monitoring system 10 principally comprises a slurry handling system 12, data analysis system 14, and sensor 16.

With reference to the FIG. 1, slurry handling system includes collection sump 18 which receives a slurry sample having a volume, for example, of about five gallons, from one of a number of slurry transport lines 20. The volume of collection sump 18 is chosen to be large enough to collect a representative sample of slurry taken from a slurry transport line by a sample cutter, which traverses the flow stream. Once the sample is introduced into collection sump 18, it is agitated by mixer 22 which provides homogeneity of the sample. From collection sump 18, the sample is brought into sample reservoir 24 which may have a volume capacity, for example, of about four gallons. Flow into sample reservoir 24 is controlled by remotely actuated valve 26. Fill sensor 27 includes a capacitance level gauge and is used to control filling of reservoir 24. Vacuum pump 28 evacuates gas in the headspace in the upper portion of sample reservoir 24 and may be one of various types including a venturi type pump. Sample reservoir 24, like reservoir 18, also includes a mixer 30 for the purpose of agitating the sample. In some configurations of systems constructed by applicants, it was found that mixer 30 can be eliminated since it has been found that recirculation of the sample during testing is sufficient to ensure adequate mixing of the sample.

At the lower end of sample reservoir 24, exit conduit 32 is provided having a first remotely actuated valve 34 which controls flow into the remainder of the slurry handling circuit, and remotely actuated valve 36 which controls dumping of the slurry mixture from sample reservoir 24 to void the system. Pump 38 is connected to conduit 32 and may be, for example, a diaphragm type pump. Pump 38 should be designed to pump slurry without causing cavitation or agitation, which could generate entrained gases. Conduit 40 is provided to transmit the slurry mixture from pump 38 and through sensor 16, and returns it to sample reservoir 24 via inlet conduit 44.

In operation, once sample reservoir 24 is filled to a predetermined level as detected by fill sensor 27, valve 26 closes, valve 34 opens, and vacuum pump 28 is energized to cause the fluid handling circuit to become evacuated, thereby causing gas bubbles entrained within the slurry to collapse. This process of applying a vacuum to the sample also causes gases dissolved in the liquid slurry to precipitate out of solution. Thereafter, pump 38 is energized to circulate the slurry within the slurry handling system 12 thereby forcing the evacuation of any remaining gas. The slurry then passes through sensor 16 at a controlled rate where it is analyzed by the data analysis system 14, as explained below.

The diameter of conduits 32, 40, and 44 (e.g. 1½ inch) and the flow rate of slurry (e.g. 30 to 40 GPM) through sensor 16 are selected to ensure that the larger coal particles which can be up to ⅜ inch in diameter are circulated along with smaller particles. The slurry is circulated over a predetermined period of time to cause the entire contents of reservoir 24 to pass through sensor 16 numerous times, which can be accomplished in a 60 to 120 second time frame. Operation in this manner ensures that all of the slurry passes through sensor 16 and is thus evaluated by the detector. After the measurements have been taken by data analysis system 14, sample reservoir 24 and the entire system is drained via valve 36. Thereafter, monitoring system 10 is available to receive another sample for analysis such that slurry from any of slurry transport lines 20 can be evaluated by a single instrument.

Sensor 16 and analyzer 14 combine to provide a means for evaluating the mineralogical composition of the slurry and particularly to determine the concentrations of ash forming minerals in the coal. Sensor 16 is a transmission type radiation detector having radiation source 46 with proportional counter 48 spaced from the source. Sensor 16 may include a block of material such as aluminum for a housing 50 which serves as a mount for source 46 and counter 48, and provides a slurry flow channel between the source and counter.

Monitoring system 10 evaluates the composition of the slurry sample using a well known relationship referred to as Lambert's law. The relationship is expressed as:

$$I = I_o \exp^{-(\mu/\rho)\rho\tau}$$

where

I = measured intensity of radiation
$I_o$ = source intensity of radiation
$\mu/\rho$ = material absorption coefficient (cm²/g)

t=distance from source (cm)

This relationship shows how gamma or X-ray radiation is attenuated by the coal slurry across a given sample distance (t). Since the mass energy absorption coefficient increases significantly with atomic number for low energy X-ray radiation, this relationship can be employed as an extremely sensitive measure of the presence of heavier ash forming elements in the coal particles. Accordingly, by measuring the attenuation of radiation in the low energy range of about 10 to 30 Kev, a signal proportional to the ash content of the coal particles is obtained.

Figure 2:
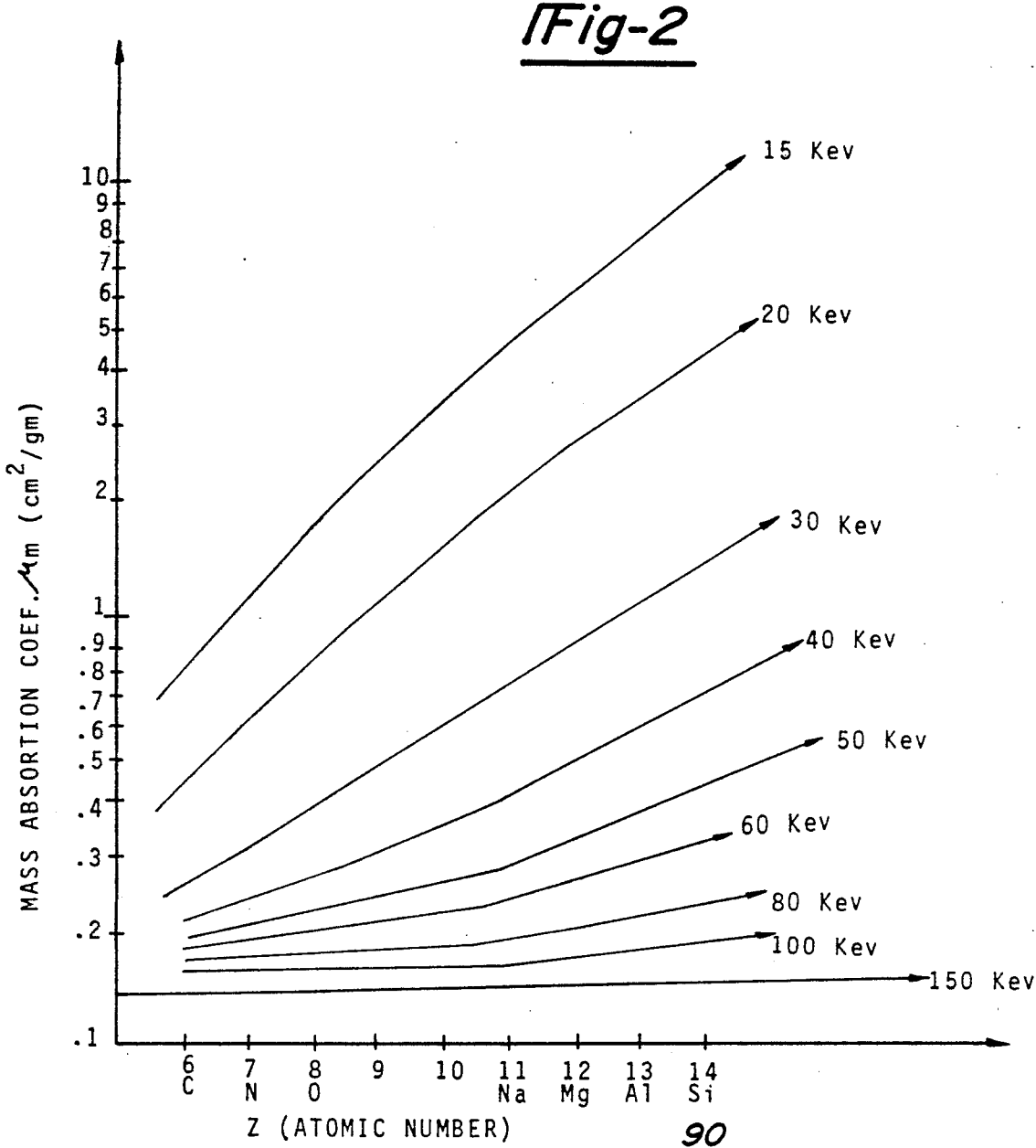
FIG. 2 is a graph showing the relationship between mass absorption and atomic number of elements found in coal slurry at various energy levels.

FIG. 2 provides an illustration of the advantages of taking gamma ray absorption measurements at a relatively low energy levels which is a departure from the approaches in accordance with the prior art. The graph of FIG. 2 shows the relationship between mass absorption coefficient plotted against the average atomic number (Z) for various elements contained in a coal slurry. Pure coal has an average value of Z=6 since it has a very high carbon content. On the other hand, the ash bearing minerals in the coal have an average Z=12, which corresponds to the oxide or carbonate state of occurrences of such elements such as magnesium, aluminum and silica. Therefore, selecting Z=6 vs Z=12 for the average atomic numbers for coal and ash respectively, one can see from FIG. 2 that a far greater change in mass absorption coefficient occurs in the 15 to 20 Kev region than for the 60 Kev region which is where prior art systems typically operate in. Accordingly, this invention employs a low energy peak of a source to provide enhanced accuracy and sensitivity since it operates along an absorption curve having a relative higher slope.

Attenuation of radiation in the slurry is attributable not only to the concentration of ash forming minerals, but also to the total concentration of particles or percent solids within the slurry. Therefore, it is necessary to determine the total quantity of coal in the slurry in order to ascertain ash content. Total coal concentration is determined by measuring gamma ray attenuation at a higher energy range, for example, in the 60 to 150 Kev range. Of all the ash forming elements, the heaviest in terms of its energy absorption coefficient is iron which is found in coal in the form of pyrite ($FeS_2$). Large variations in iron concentration can disproportionately skew the measured concentration of ash forming minerals. Therefore, to provide enhanced system accuracy, the total quantity of iron in the coal mixture is measured independently. Such measurement can be readily done by selecting a source whereby $K\alpha$ X-rays can be excited and subsequently measured by the system. These X-rays are generated when exited iron electrons return to a lower energy level, giving off a photon of X-rays of a characteristic energy. This technique can also be used to determine iron concentrations in materials other than coal slurry, such as iron ore slurries.

In order to provide the above mentioned measurements, a suitable radiation source must be selected. Such source can be either a single element source or a multiple element source, depending on system configuration and design. The source must provide a minimum of three characteristic detected peaks which are related to iron, ash and total solids content. Sources would be selected on the basis of their half-life, photon emission rates, and energy spectra. One suitable single source is Americium-241. A representative emission spectrum for an Americium-241 source is provided by FIG. 3 which relates counted events versus energy. Curve 52 traces the emission spectrum of the source and shows peaks 54 (Np $L\alpha$ X-ray) and 56 (Am 241 X-ray) at about 20 and 60 Kev's, respectively. Other sources such as Cd-109, Te-123, Y-88, Cm-244, Pb-210, or Pu-238 could be used for providing ash-related signals, and a Gd-153 source would provide the density related signal. Two or more of these radiation source materials can be mixed together to provide a a radiation source having the desired emission spectrum.

Proportional counter 48 is designed such that a complete spectrum within the range of zero to one hundred Kev's or greater can be detected without a significant loss in counting efficiency at the higher end of the energy range. The selection of counter 48 is dictated by the source used. If a broad range of characteristic peaks are to be measured, a scintillation type detector may be required.

The slurry is exposed to X and gamma ray bombardment within sensor 16. The source is mounted directly in line with the detector, and if multiple source materials are required, one can be mounted inside of the other (the outside source having a ring configuration) or they can be mixed together as mentioned above. The distance between the source and the detector is determined by the relationship given above for computing gamma or X-ray attenuation. This distance (t) is dependent on the source selected and the ranges of solids and ash contents in the slurries to be measured. Both source 46 and counter 48 are counted to the ends of housing 50. A mylar window may be used as an interface between source 46 and the slurry, and also between counter 48 and the slurry. In some applications, housing 50 may be constructed of a low density polymer and mylar windows would not be required.

Proportional counter 48 produces pulses upon exposure to radiation emissions and relies on the phenomenon of gas multiplication to amplify the charge represented by ion pairs created within a gas chamber. The resultant signal is processed by preamplifier 58, amplifier 60, and multi-channel analzyer 64. The signal then is processed through an analog-to-digital conversion device and a computer RS-232 serial interface 66, and the information is then inputted to computer 68 where calibration curves for density, ash, and iron correction are stored. From these data, ash and density values are computed along with a pyritic sulfur value (which is directly proportional to the iron count rate, purite being $FeS_2$ and the only significant iron-bearing mineral in the ash). The methodology for making these determinations is outlined below.

Figure 3:
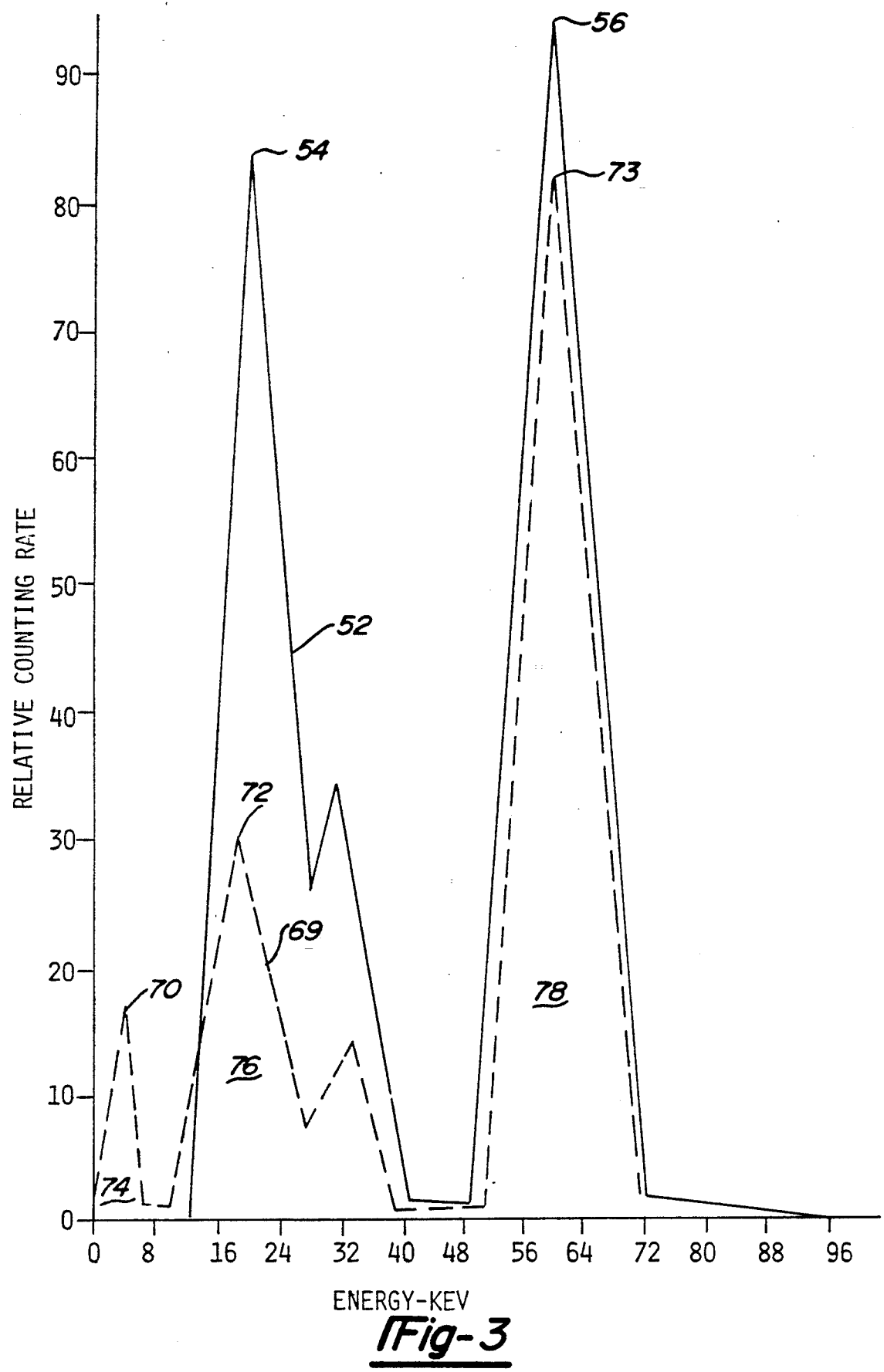
FIG. 3 shows the emission spectra of an exemplary radiation source of the detection system used with the system of this invention, shown with a received spectra showing attenuation and stimulated emissions caused by the presence of elements of the slurry.

FIG. 3 shows the emission spectrum represented by curve 52 of an Americium-241 source. Superimposed in this figure is the resulting detected spectrum designated by curve 69 that would be measured by counter 48 once the radiation has been transmitted through the slurry sample. There are three characteristic peaks of interest in the example shown. The first peak is an iron $K\alpha$ X-ray peak at 6.4 Kev, identified by reference member 70. The second peak 72 occurs at between 12 and 20 Kev's and is related to absorption by ash forming minerals. The third peak 73 is an Americium-241 gamma peak at 59.6 Kev's which is related to solids concentration. These peaks occur within regions of interest beneath curve 69, identified by reference numbers 74, 76 and 78. Total counts under each of the peaks are accumulated by integrating the area under the peaks, and the ash value is computed via an equation of the form:

$$\%Ash = a + b(CT1) + c(CT2) + d(CT3) + e[(CT2)(CT3)]^2$$

where, CT1, CT2 and CT3 = Accumulated counts under peaks 70, 72 and 73, respectively, and a, b, c, d, and e are empirically determined constants.

An alternative to using the above equation is to generate independent calibration curves for the density, ash and iron components. The specific terms in the equation and the forms of the equations are dictated by the number of peaks measured and the functional relationship of ash and density in a particular application.

In addition to performing a signal processing function, computer 68 also controls the overall system by controlling valves 26, 34, and 36, and pumps 28 and 38 in response to internal commands and external inputs, including an input from fill sensor 27.

The system 10 described above is capable of providing near-real time measurements of slurry composition from plural sources, and as mentioned above, provides excellent accuracy due to a reduction of entrained gas bubbles, and by measuring a homogeneous slurry mixture.

Figure 4:
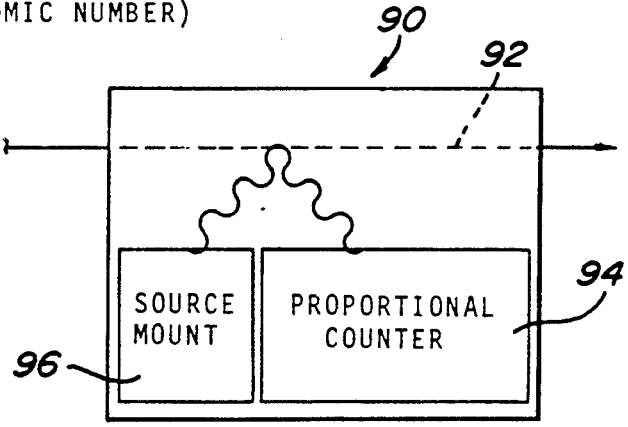
FIG. 4 is a pictorial view of an alternate embodiment of a sensor for use in the system of FIG. 1 for measuring the concentration of iron pyrite in the sample.

Now with reference to FIG. 4, an iron concentration sensor is shown which is designated by reference number 90. This sensor is modified from that shown in FIG. 1 such that the radiation source 96 is on the same side of the flow stream 92 as the counter 94. This configuration enables very accurate detection of the very low energy K$\alpha$ X-ray peak at 6.4 Kev. This is possible since the radiation does not have to pass a long distance through the slurry sample in the test cell before it is reflected or back-scattered to the counter. When the source is on the same side of the pipe or flow cell as the counter, a certain fraction of the photons that leave the source interact with the particles in the slurry, producing characteristic X-rays which do not have to travel through the entire flow stream and, thus, can be detected through a thin window of polyethylene or mylar. Stimulated emissions associated with material other than iron can also be detected for an analyses system for slurries in accordance with this invention.

Sensor 90 is not used to detect percent solids in the slurry, rather this alternate embodiment would preferably be used in conjunction with sensor 16 which was previously described. This embodiment of sensor 90 has the limitation that the radiation does not "see" as much of the slurry since what comes back to detector has not passed through the entire flow stream 92. However, this arrangement is useful for determining the iron content in the ash which can correlated to the pyritic iron content in the coal and is used as correction factor in cases in where the iron concentration of the ash varies considerably.

While the above description constitutes the preferred embodiments of the present invention, it will be appreciated that the invention is susceptible to modification, variation and change without departing from the proper scope and fair meaning of the accompanying claims.

We claim:

1. A system for evaluating the composition of a slurry comprising:
   a sample reservoir for containing a sample of slurry wherein the slurry may contain a plurality of entrained gas bubbles,
   slurry control and transport means for enabling said sample reservoir to be filled and drained of the slurry and for sealing said sample reservoir to define a closed volume,
   sensor means for measuring radiation attenuation associated with the slurry for evaluating the slurry composition,
   slurry pump means for pumping the slurry,
   conduit means for removing the slurry from said sample reservoir through actuation of said slurry pump means, and for transporting the slurry to said sensor means, and for returning the slurry to said sample reservoir wherein the slurry is transmitted through said sensor means and returned to said sample reservoir as said slurry control and transport means seals said sample reservoir to define a closed volume, and
   a vacuum pump for evacuating said sample reservoir thereby reducing the amount of said entrained gas bubbles within the slurry thereby enhancing the accuracy of said evaluation by said sensor means.

2. A system for evaluating the composition of a slurry as in claim 1 further comprising a mixer in said sample reservoir for agitating the slurry.

3. A system for evaluating the composition of a slurry as in claim 1 wherein said sensor means evaluates said composition by analyzing the interaction between radiation emissions and the slurry.

4. A system for evaluating the composition of a slurry as in claim 3 wherein said sensor means includes a radiation source and a detector for sensing the transmission of radiation from said source passing through the slurry.

5. A system for evaluating the composition of a slurry as in claim 1 wherein the slurry is a fine coal and liquid mixture.

6. A system for evaluating the composition of a slurry as in claim 1 wherein said slurry control and transport means includes a first valve which controls flow of the slurry to said sample reservoir and a second valve for controlling the flow of the slurry through said sensor means and a third valve for permitting the slurry to be drained from said sample reservoir.

7. A system for evaluating the composition of a slurry as in claim 1 further comprising a collection sump for receiving a sample of the slurry and retaining said sample prior to introduction into said sample reservoir.

8. A system for evaluating the composition of a slurry as in claim 7 wherein said collection sump accepts said samples from a plurality of slurry transfer lines.

9. A system for evaluating the composition of a slurry as in claim 1 further comprising controller means for controlling the filling of said sample reservoir with the slurry, and actuating said vacuum pump and said slurry pump means.

10. A system for evaluating the composition of a slurry as in claim 1 wherein said slurry pump means comprises a positive displacement type pump.

11. A system for evaluating the composition of a slurry as in claim 1 wherein said sensor means includes a radiation source having an output in the ranges of about 10–30 Kev and about 60–150 Kev, said sensor means further includes a radiation counter which detects the absorption of radiation as said radiation passes through the slurry wherein the concentration of ash producing element within the slurry is evaluated through measuring the attenuation of radiation at about 10–30 Kev which is related to the concentration of ash forming minerals in the slurry, and the attenuation of the radiation at about 60–150 Kev which is related to the concentration of total solids in the slurry.

12. A system for evaluating the composition of a slurry as in claim 11 wherein said radiation counter further detects an output at about 6.4 Kev, related to emissions from iron pyrite in the slurry enabling the computation of an iron correction factor in the ash determination.

13. A system for evaluating the composition of a coal slurry comprising:
   a collection sump for receiving a sample of the slurry,
   a sample reservoir for receiving the slurry from said collection sump and for containing said sample of slurry wherein the slurry may contain a plurality of entrained gas bubbles,
   first valve means for permitting the slurry to end said sample reservoir from said collection sump and for stopping the flow of the slurry from said collection sump and sealing said sample reservoir to define a closed volume,
   slurry pump means for pumping the slurry,
   sensor means which measures radiation attenuation associated with the slurry for evaluating the mineralogical composition of the slurry,
   second valve means for controlling flow of the slurry out of said sample reservoir and through said sensor means,
   third valve means for controlling draining of the slurry out of said sample reservoir, and for sealing said sample reservoir to define a closed volume,
   conduit means for removing the slurry from said sample reservoir upon actuation of said slurry pump means, and for transporting the slurry through said sensor means and for recirculating the slurry back to said sample reservoir wherein the slurry is transmitted to said sensor means and returned to said sample reservoir,
   a vacuum pump for evacuating said sample reservoir as said first and third valve means are closed to seal said sample reservoir thereby reducing the amount of entrained gas bubbles within the slurry, and
   controller means for controlling said first valve means to fill said sample reservoir from said collection sump, for actuating said second and third valve means to define a closed volume for said sample reservoir, for energizing said vacuum pump, for opening said second valve means, and for energizing said slurry pump means for circulating the slurry through said sensor means and thereafter actuating said third valve means to drain said sample reservoir.

14. A system for evaluating the composition of a coal slurry as in claim 13 further comprising a mixer in said sample reservoir for agitating the slurry.

15. A system for evaluating the composition of a coal slurry as in claim 13 wherein said sensor means evaluates the composition of the slurry by analyzing the interaction between radiation emissions and the slurry.

16. A system for evaluating the composition of a coal slurry as in claim 15 wherein said sensor means includes a radiation source and a detector for sensing the transmission of radiation from said source passing through the slurry.

17. A system for evaluating the composition of a coal slurry as in claim 13 wherein said collection sump accepts said samples from a plurality of slurry transfer lines.

18. A system for evaluating the composition of a coal slurry as in claim 13 wherein said slurry pump means comprises a positive displacement type pump.

19. A system for evaluating the composition of a coal slurry as in claim 13 wherein said sensor means includes a radiation source having an output in the ranges of about 10–30 Kev and about 60–150 Kev, said sensor means further includes a radiation counter which detects the absorption of radiation as said radiation passes through said slurry wherein the concentration of ash producing element within the slurry is evaluated through measuring attenuation of radiation at about 10–30 Kev which is related to the concentration of ash forming minerals of the slurry, and the attenuation of the radiation at about 60–150 Kev which is related to the concentration of total solids in the slurry.

20. A system for evaluating the composition of a coal slurry as in claim 19 wherein said radiation counter further detects an output at about 6.4 Kev, related to emissions from iron pyrite in the slurry enabling the computation of an iron correction factor in the ash determination.

* * * * *

UNITED STATES PATENT AND TRADEMARK OFFICE
CERTIFICATE OF CORRECTION

PATENT NO. : 5,065,416

DATED : November 12, 1991

INVENTOR(S) : Laurila et al.

It is certified that error appears in the above-identified patent and that said Letters Patent is hereby corrected as shown below:

Column 3, line 47, (application page 7, line 4), after "system" the number --12-- should be indicated.

Column 9, line 16, Claim 13 (Amendment dated 5-29-91 page 3, line 1, Claim 14) "end" should read as --enter--.

Signed and Sealed this

Fourth Day of May, 1993

Attest:

MICHAEL K. KIRK

Attesting Officer

Acting Commissioner of Patents and Trademarks